(12) United States Patent
Huang et al.

(10) Patent No.: US 7,597,791 B2
(45) Date of Patent: Oct. 6, 2009

(54) METHOD AND APPARATUS FOR GENERATING ELECTRIC FIELDS AND FLOW DISTRIBUTIONS FOR RAPIDLY SEPARATING MOLECULES

(75) Inventors: Lotien Richard Huang, Brookline, MA (US); James Christopher Sturm, Princeton, NJ (US); Robert Hamilton Austin, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 155 days.

(21) Appl. No.: 10/147,370

(22) Filed: May 15, 2002

(65) Prior Publication Data
US 2003/0075444 A1    Apr. 24, 2003

Related U.S. Application Data

(60) Provisional application No. 60/343,152, filed on Oct. 19, 2001, provisional application No. 60/343,150, filed on Oct. 19, 2001.

(51) Int. Cl.
*G01N 27/453* (2006.01)
(52) U.S. Cl. .................. 204/600; 204/450; 422/100
(58) Field of Classification Search .................. 204/600, 204/450, 643, 547; 422/100
See application file for complete search history.

(56) References Cited

U.S. PATENT DOCUMENTS

| | | | |
|---|---|---|---|
| 2,555,487 A | 6/1951 | Haugaard, et al. |
| 3,450,624 A | 6/1969 | Natelson |
| 3,458,427 A | 7/1969 | Strickler |
| 3,498,905 A | 3/1970 | Strickler |
| 3,519,549 A | 7/1970 | Grassmann, et al. |
| 3,563,872 A | 2/1971 | Huebner |
| 3,847,773 A | 11/1974 | Snyder |
| 4,061,560 A | 12/1977 | Hannig et al. |
| 4,148,703 A | 4/1979 | Trop et al. |
| 4,315,812 A | 2/1982 | Karlson |

(Continued)

FOREIGN PATENT DOCUMENTS

EP     0560974 B1    1/1997

(Continued)

OTHER PUBLICATIONS

Manz et al, J. Micromech. Microeng. 4 (1994), pp. 257-265.*

(Continued)

*Primary Examiner*—Kaj K Olsen
(74) *Attorney, Agent, or Firm*—McCarter & English, LLP

(57) ABSTRACT

A method and apparatus for generating tunable, uniform electric fields in fluidic applications for rapid separation of molecules, such as DNA, is provided. A region receives the molecules to be separated, the molecules being injected into the region by an injection channel connected thereto. Fluidic microchannels or resistor arrays connected to sides of the region inject currents into the region and produce electric fields in the region that can be oriented at any angle. The electric fields can separate the molecules according to size, and can be used to move or manipulate the molecules within the region. Further, the molecules can be separated by controlling fluid flows within the region to manipulate the molecules. One or more reservoirs can be attached to the fluidic microchannels for collecting the molecules after separation, movement, or manipulation.

42 Claims, 15 Drawing Sheets

U.S. PATENT DOCUMENTS

| | | | |
|---|---|---|---|
| 4,473,452 | A | 9/1984 | Cantor et al. |
| 4,523,320 | A | 6/1985 | Stappaerts |
| 4,693,804 | A | 9/1987 | Serwer |
| 4,732,656 | A | 3/1988 | Hurd |
| 4,737,251 | A | 4/1988 | Carle et al. |
| 4,740,283 | A | 4/1988 | Laas et al. |
| 4,830,726 | A | 5/1989 | Stamato et al. |
| 5,011,586 | A | 4/1991 | Finney et al. |
| 5,084,157 | A | 1/1992 | Clark et al. |
| 5,106,468 | A | 4/1992 | Chimenti |
| 5,116,471 | A | 5/1992 | Chien et al. |
| 5,122,248 | A | 6/1992 | Karger et al. |
| 5,165,898 | A | 11/1992 | Chu et al. |
| 5,178,737 | A | 1/1993 | Lai |
| 5,180,480 | A | 1/1993 | Manz |
| 5,405,519 | A | 4/1995 | Schwartz |
| 5,427,663 | A | 6/1995 | Austin et al. |
| 5,671,086 | A | 9/1997 | Parvin et al. |
| 5,837,115 | A | 11/1998 | Austin et al. |
| 5,972,190 | A | 10/1999 | Richman |
| 6,027,623 | A | 2/2000 | Ohkawa |
| 6,110,339 | A | 8/2000 | Yager et al. |
| 6,156,273 | A | 12/2000 | Regnier et al. |
| 6,176,990 | B1 | 1/2001 | Yager et al. |
| 6,254,754 | B1 | 7/2001 | Ross et al. |
| 6,280,590 | B1 | 8/2001 | Cheng et al. |
| 6,328,868 | B1 | 12/2001 | Weber |
| 6,540,896 | B1 * | 4/2003 | Manz et al. .................. 204/451 |
| 6,596,144 | B1 | 7/2003 | Regnier et al. |
| 6,685,810 | B2 | 2/2004 | Noca et al. |
| 6,881,317 | B2 | 4/2005 | Huang et al. |
| 2005/0161331 | A1 | 7/2005 | Huang et al. |

FOREIGN PATENT DOCUMENTS

| | | |
|---|---|---|
| WO | WO 02/50095 A1 | 6/2002 |
| WO | WO 03/035228 A1 | 5/2003 |

OTHER PUBLICATIONS

Huang, et al., "Generation of Large-Area Tunable Uniform Electric Fields in Microfluidic Arrays for Rapid DNA Separation," Technical Digest of the International Electron Devices Meeting, pp. 363-366, (2001).

Bakajin, et al., "Microfabricated Arrays for Fractionation of Large DNA Molecules Via Pulsed Field Electrophoresis," Biological Physics: Third International Symposium, 1999, pp. 243-248.

Duke, et al., "Microfabricated Sieve for the Continuous Sorting of Macromolecules," Physical Review Letters, vol. 80, No. 7, Feb. 16, 1998, pp. 1552-1555.

Duke, et al., "Pulsed-Field Electrophoresis in Microlithographic Arrays," Electrophoresis, vol. 17, 1996, pp. 1075-1079.

Viovy, "Electrophoresis of DNA and Other Polyelectrolytes: Physical Mechanisms," Views of Modern Physics, vol. 72, No. 3, Jul. 2000, pp. 813-872.

PCT International Search Report mailed Dec. 17. 2002, in connection with International Publication No, WO 03/035228 A1.

PCT Written Opinion mailed Sep. 25, 2003, in connection with International Publication No. WO 03/035228 A1.

PCT international Preliminary Examination Report completed Jan. 22, 2004, in connection with International Publication No, WO 03/035228 A1.

PCT International Search Report mailed Apr. 19, 2002, connection with International Publication No. WO 02/50095 A1.

PCt Written Opinion mailed Apr. 17, 2003, in connection with International Publication No, WO 02/50095 A1.

PCT International Preliminary Examination Report completed Jun. 2004, in connection with International Publication No. WO 02/50095 A1.

European Search Report dated May 18, 2005 in connection with European Application No. EP 01 99 1239.

Notice of Allowance dated Dec. 14, 2004 from U.S. Patent No. 6,881,317.

Office Action dated Feb. 23, 2004, from U.S. Patent No. 6,881,317.

Office Action dated Aug. 20, 2003, from U.S. Patent No, 6,881,317.

Office Action dated Mar. 24, 2003, from U.S. Patent No. 6,881,317.

Notice of Allowance dated Nov. 9, 2007 from pending U.S. Appl. No. 11/075,682.

Office Action dated Oct. 10, 2007, from pending U.S. Appl. No. 11/015,682.

Office Action dated Jun. 20, 2007, from pending U.S. Appl. No. 11/075,682.

Advisory Action dated Apr. 19, 2007, from pending U.S. Appl. No. 11/075,682.

Inteview Summary dated Apr. 10, 2007, from pending U.S. Appl. No. 11/075,682.

Office Action dated Dec. 12, 2006, from pending U.S. Appl. No. 11/075,682.

Office Action dated Aug. 25, 2006, from pending U.S. Appl. No. 11/075,682.

Office Action dated Feb. 7, 2006, from pending U.S. Appl. No. 11/075,682.

Notice of Allowance and Fees Due mailed Mar. 20, 2008 from co-pending U.S. Appl. No. 11/075,682.

Notice of Allowability mailed Mar. 20, 2008 from co-pending U.S. Appl. No. 11/075,682.

Office Action dated Jul. 22, 2008, issued by Japanese Patent Office in connection with pending Japanese Patent Application No. 2002-551988 (3 pages).

English translation of Office Action dated Jul. 22, 2008, issued by Japanese Patent Office in connection with pending Japanese Patent Application No. 2002-551988 (3 pages).

Beverley, "Characterization of the 'unusual' mobility of large circular DNAs in pulsed field-gradient electrophoresis", Nucleic Acids Research, 1988, pp. 925-939, vol. 16, No. 3 (15 pages).

Office Action dated Aug. 20, 2008, issued by the European Patent Office in connection with European Patent Application No. 09 991 239. 3-2204 (6 pages).

Beverley, "Characterization of the 'Unusual' Mobility of Large Circular DNAs in Pulsed Field-Gradient Electrophoresis," Nucleic Acids Research, vol. 16, No. 3, (1988) pp. 925-939 (15 pages).

Cognasso, et al., "L' elettroforesi su carta in corrente alternata asimmetrica," Progresso Medico, vol. XVII, No. 8, Apr. 30, 1961, pp. 255-258 (5 pages) (including English summary).

Schwartz, et al., "Separation of Yeast Chromosome-Sized DNAs by Pulsed Field Gradient Gel Electrophoresis," Cell, vol. 37, May 1984. pp. 67-75 (9 pages).

Van der Ploeg, et al., "Antigenic Variation in Trypanosoma Brucei Analyzed by Electrophoretic Separation of Chromsome-Sized DNA Molecules," Cell, vol. 37, May 1984, pp. 77-84 (8 pages).

McPeek, et al., "Separation of Large DNA Molecules by Modified Pulsed Field Gradient Gel Electrophoresis," Analytical Biochemistry, (1986) 156, pp. 274-285 (12 pages).

Borst, et al., "Structure of Amplified DNA, Analyzed by Pulsed Field Gradient Gel Electrophoresis," Journal of Cellular Biochemistry, (1987) 34, pp. 247-258 (12 pages).

Riveron, et al., "Un prototipo para la electroforesis de campo pulsante. Estandarización de las condiciones para la resolución de grandes moléculas de ADN," Interferón y Biotecnologia, vol. 5, No. 1, (1988) pp. 66-76 (6 pages) (including English summary).

Dawkins, "Large DNA Separation Using Field Alternation AGAR Gel Electrophoresis," Journal of Chromatography, 492 (1989) pp. 615-639 (25 pages).

Akerman, et al., "Reorientational Dynamics and Mobility of DNA During Pulsed-Field Agarose Gel Electrophoresis," Journal of Physical Chemistry, (1990), 94, pp. 3828-3838 (11 pages).

Norden, et al., "Electrophoretic Orientation of DNA," Int. Conf. Electrophor., Supercomput. Hum. Genome, 1st 1991, Meeting Date 1990, pp. 173-198, Editors: Cantor, C. R. et al., Publisher: World Sci., Singapore, Singapore (26 pages).

Lai, et al., "Rapid Restriction Map Constructions Using a Modified pWE15 Cosmid Vector and a Robotic Workstation," BioTechniques, vol. 11, No. 2 (1991), pp. 212-214, 216-217 (5 pages).

Burmeister, "PFGE Using Double-Inhomogeneous Fields or Orthogonal Field-Alternating Gel Electrophoresis (Ofage)," Methods in Molecular Biology, vol. 12 (1992), pp. 39-49 (11 pages).

Slater, et al., "Bidirectrional Transport of Polyelectrolytes Using Self-Modulating Entropic Ratchets," Physical Review Letters, vol. 78, No. 6, Feb. 10, 1997, pp. 1170-1173 (4 pages).

Gorre-Talini, et al., "Dielectrophoretic Ratchets," Chaos, vol. 8, No. 3, Sep. 1998, pp. 650-656 (7 pages).

Desruisseaux, et al., "Trapping Electrophoresis and Ratchets: a Theoretical Study for DNA-Protein Complexes," Biophysical Journal, vol. 75, Sep. 1998, pp. 1228-1236 (9 pages).

Van Oudenaarden, et al., "Brownian Ratchets: Molecular Separations in Lipid Bilayers Supported on Patterned Arrays," Science, vol. 285, Aug. 13, 1999, pp. 1046-1048 (3 pages).

Chou, et al., "Sorting by Diffusion: an Asymmetric Obstacle Course for Continuous Molecular Separation," Proceedings of the National Academy of Sciences of the United States of America, vol. 96, No. 24, Nov. 23, 1999, pp. 13762-13765 (4 pages).

Office Action dated Mar. 5, 2009, from pending U.S. Appl. No. 11/075,682 (14 pages)

* cited by examiner

METHOD AND APPARATUS FOR GENERATING ELECTRIC FIELDS AND FLOW DISTRIBUTIONS FOR RAPIDLY SEPARATING MOLECULES

RELATED APPLICATIONS

This application claims the benefit of U.S. Provisional Application Ser. No. 60/343,152 filed Oct. 19, 2001, and U.S. Provisional Application Ser. No. 60/343,150 filed Oct. 19, 2001, the entire disclosures of which are both expressly incorporated herein by reference.

STATEMENT OF GOVERNMENT INTERESTS

This invention was made with government support under Contract No. MDA 972-00-1-0031. The government has certain rights in this invention.

BACKGROUND OF THE INVENTION

1. Field of the Invention

The present invention relates generally to molecule separation techniques, and more specifically, to a method and apparatus for rapidly separating molecules, such as genomic DNA, using electric fields and flow distributions.

2. Related Art

The control of electric fields over large areas in fluidic systems is crucial for the accurate delivery and manipulation of biologically important molecules, such as DNA. Most biologically important molecules, including proteins, are electrically charged. Previous attempts at controlling such molecules involved manipulating same on a microscopic scale using electric fields. For example, in a method known as electrophoresis, charged molecules are migrated through a fluid under the influence of an applied electric field. In pulsed-field gel electrophoresis ("PFGE"), DNA of different sizes can be separated by alternating between uniform fields in different directions across a two-dimensional area of typically 30 cm×30 cm.

In principle, one can use two pairs of electrodes to create tunable fields in a two-dimensional area, one pair for each field component (i.e., vertical or horizontal directions). However, the resulting field is highly distorted, because the electrodes perturb the fields generated thereby. In conventional PFGE systems, this problem is solved by a method that uses many electrodes to clamp the electric potential along a closed contour, known as a contour-clamped homogenous electric field ("CHEF") method. Fundamentally, this is equivalent to imposing a Dirichlet boundary condition to the Laplace equation governing the electric field. However, the CHEF method is inappropriate for fluidic applications where the array is only ~1 cm×1 cm, because electrodes thereof can interfere with other functions of the array, such as sample loading and extraction. Further, such systems are not effective—even with the 24 electrodes typically used in commercial PFGE apparatuses, the field near the electrodes is not uniform. Additionally, microelectrodes inside fluidic channels are susceptible to erosion and bubble generation.

In the area of fluidic devices, and more particularly, in systems used in electrophoresis, it is desirable that the applied electric field in a layer of electrolyte be uniform. This is particularly true in traditional gel electrophoresis, which is used to assay proteins or nucleic acids, wherein many test samples are run simultaneously and/or in parallel. Non-uniformity of the electric field in a gel slab of such systems can cause a detrimental "smile effect," which makes analysis of samples difficult and/or unreliable. Further, in PFGE, which can be used to fractionate large nucleic acids, not only does the electric field have to be homogenous, but the direction of the field must alternate with respect to the gel slab. Therefore, the ability to generate uniform electric fields in two-dimensional arrays, in addition to the ability to change the direction of such fields, is of paramount importance.

In CHEF systems, such as the system shown in FIG. 1$a$, complex electric fields having no divergence or curl can be generated in the layer of electrolyte using the plurality of electrodes to define an electric potential along a contour. Once the electric potential at each point of the boundary is set (i.e., at each of the electrodes), a Dirichlet boundary condition is established, with the electric potential $\Phi$ and the electric field E in the enclosed region of the electrolyte determined by the equations $\nabla^2\Phi=0$ and $E=-\nabla\Phi$ when there is no current source (i.e., no electrode) inside the region.

Such an application, however, is not practical for small array applications, because different voltages must be applied to different locations and/or electrodes. Further, this approach requires numerous electrodes, electrolyte reservoirs, and complex driving circuits. Additionally, the method of FIG. 1$a$ is inappropriate for micro-electrophoretic applications, because microfluidic devices are vulnerable to bubbles generated at the electrolyte/electrode interface inside the device.

Also in the area of fluidic devices, it is desirable to control the flow distribution of a layer of liquid contained therein. A common characteristic of such devices is that the Reynold's number of the fluid inside the device is so small that the flow is always laminar, i.e., non-turbulent. Also, because the layer of fluid is very thin, flow profiles that are usually parabolic can be ignored, and flow can be described in terms of its average flow velocity as a function of two position coordinates, for example, x and y. In addition, it can be assumed that the thickness of the fluid layer is so small that the overall shear force on each fluid element is dominated by the viscous shear between the fluid and the walls of the device. Viscous shear between any two fluid elements that are in different positions can be neglected. Therefore, the current J of the liquid flow is proportional to the negative gradient of the pressure P; that is, $J=-\sigma\nabla P$, wherein $\sigma$ is the conductance tensor. Because liquid is incompressible, the current has no divergence, and the equation that describes the flow distribution is $\nabla^2 P=0$.

In flow distribution systems presently used in the art, such as the system shown in FIG. 1$b$, a plurality of contact holes connected to exterior pressure regulators are provided near the perimeter of a region containing, for example, a fluid. This methodology allows for the control of flow distributions of the fluid, because Dirichlet boundary conditions thereof determine the solutions to Laplace equations. Such a system, however, is not practical for fluidic applications, because different pressures have to be applied to different locations, and numerous pressure sources are required.

What would be desirable, but has not yet been provided, is a technique that solves the above shortcomings while providing rapid separation of molecules. What would also be desirable, but has not yet been provided, is a method and apparatus for generating uniform electric fields and flow distributions for rapidly separating molecules.

OBJECTS AND SUMMARY OF THE INVENTION

It is an object of the present invention to provide a method and apparatus for generating electric fields using current injectors for rapidly separating molecules.

It is a further object of the present invention to provide a method and apparatus for generating flow distributions using fluidic microchannels for rapidly separating molecules.

It is another object of the present invention to provide a current injection method for rapidly separating and/or moving molecules by applying tunable, uniform, alternating electric fields to two dimensional arrays.

It is a further object of the present invention to provide a molecule separation and movement device capable of producing uniform fields without requiring the presence of electrodes in fluidic microchannels or regions of the device.

It is yet another object of the present invention to provide a molecule separation and movement method and apparatus that includes microchannels for sample injection and extraction.

It is still another object of the present invention to provide a molecule separation and movement device that can be microfabricated.

The present invention relates to a method and apparatus for generating electric fields and flow distributions in fluidic arrays for rapid separation and movement of molecules, such as DNA molecules. Electric fields generated in a two-dimensional region (i.e., a chamber, matrix, array, or structure having microposts, etc.) allow for the separation and/or movement of the molecules according to size. In one embodiment of the invention, arrays of resistors connected in parallel to voltage sources on each side of the region allow for the injection of current therein, creating uniform electric fields in the region that can be oriented at any desired angle to separate the molecules. In another embodiment, fluidic channels, such as fluidic microchannels, that act as resistors are connected in parallel along sides of the region to voltage sources for injecting current into the region, the current establishing the uniform electric fields and separating and/or moving the molecules at the desired angle. In another embodiment, the fluidic microchannels produce uniform flow distributions of fluids in the region which are capable of being oriented at any desired angle. In this case, molecule movement and/or separation can take place without electric fields. One or more injection channels can be provided for injecting molecules into the region, and the fluidic microchannels surrounding the region can extract molecules from the region and deliver same to one or more reservoirs when separation and/or movement of the molecules occurs. A device according to the invention can be microfabricated from a fused silica substrate in one lithographic step, and operates at orders of magnitude faster than conventional systems.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The present invention relates to a method and apparatus for generating electric fields and flow distributions in fluidic arrays for rapid separation of molecules, such as DNA. Electric currents are injected into a two-dimensional region (i.e., a chamber, matrix, array, or other structure having microposts, etc.), allowing the molecules to be separated and/or moved according to size. The fields are established by current injection using arrays of resistors or fluidic channels connected to sides of the region. Flow distributions can be generated in the region using fluidic microchannels without an electric field to move and/or separate molecules. Optionally, the separated molecules can be channeled into one or more reservoirs connected to the region via the fluidic microchannels. The invention can be microfabricated on fused silica glass, operates at orders of magnitude faster than conventional methods, and can be utilized to detect diffusions coefficients, or other properties of molecules.

Figure 2:
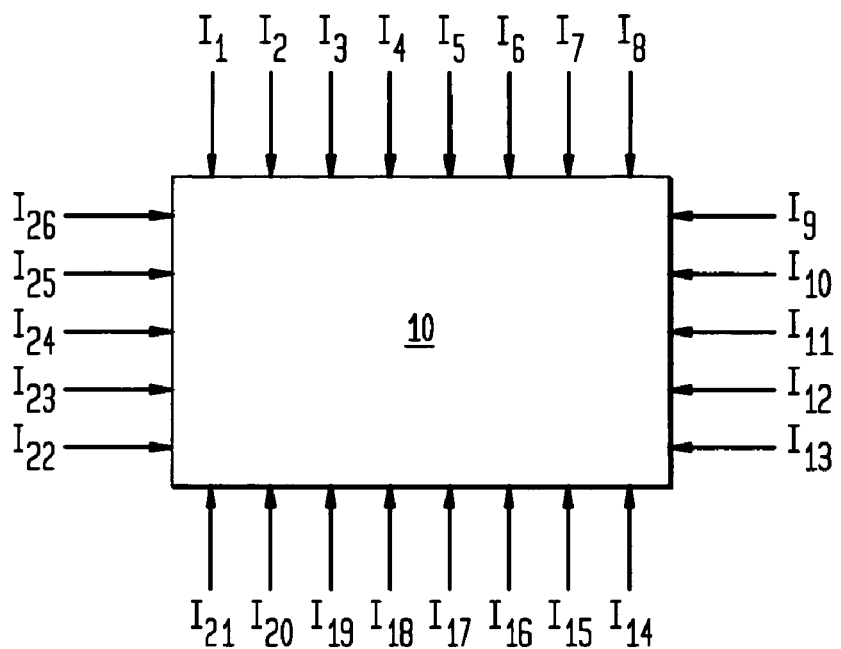
FIG. 2 is a diagram showing a region utilizing current injection techniques of the present invention.

FIG. 2 is a diagram showing a region (i.e., matrix, two-dimensional array, chamber, or other structure) utilizing current injection techniques of the present invention. It is to be understood that the methods disclosed herein can be applied to generate electric fields of all types, such as large-area, tunable, and uniform electric fields. For purposes of illustration, however, the generation of uniform electric fields is discussed herein. Region 10 is a two-dimensional region of a layer of fluid or electrolyte wherein it is desired to introduce an electric field. No electrode or magnetic field is present within region 10, nor are fluid drains or sources present therein. According to Maxwell equations, the absence of a current source, electrodes, and magnetic fields within region 10 implies that the electric field generated within region 10 will have no divergence or curl. Therefore, the electric potential $\Phi$ and the electric field E of the layer of electrolyte is governed by the equations $E=-\nabla\Phi$ and $\nabla^2\Phi=0$. Additionally, the current density of the flow J of liquid within region 10 is proportional to the gradient of the pressure, wherein $J=-\sigma\nabla P$, and $\sigma$ is the conductance tensor. The absence of a fluid source or drain within region 10 implies that $\nabla^2 P=0$. The pressure inside the region 10 satisfies Laplace's equation.

A variety of boundary conditions can be utilized to determine the electric field within region 10, such as Dirichlet boundary conditions, Neumann boundary conditions, and Cauchy boundary conditions. In a preferred embodiment of the present invention, Neumann boundary conditions are used to generate a desired electric field or flow distribution within region 10. A normal component of the current density at each point of the boundary of region 10 is specified into the enclosed, two-dimensional region region 10 with a plurality of current sources, indicated illustratively as current sources $I_1$ through $I_{26}$. It is to be understood that fewer or greater that the number of current sources shown in FIG. 2 can be utilized without departing from the scope of the present invention. Each of the current sources controls only the normal component (with respect to the boundary) of the current that is injected into or extracted from the region 10, thereby satisfying the requirements of a Neumann boundary condition.

In order to generate a uniform electric field, it is necessary to determine the normal component of the current at each point of the boundary of region 10. A superposition principle can then be used to determine the field distribution of region 10. Such a process is described in FIGS. 3-5.

Figure 3:
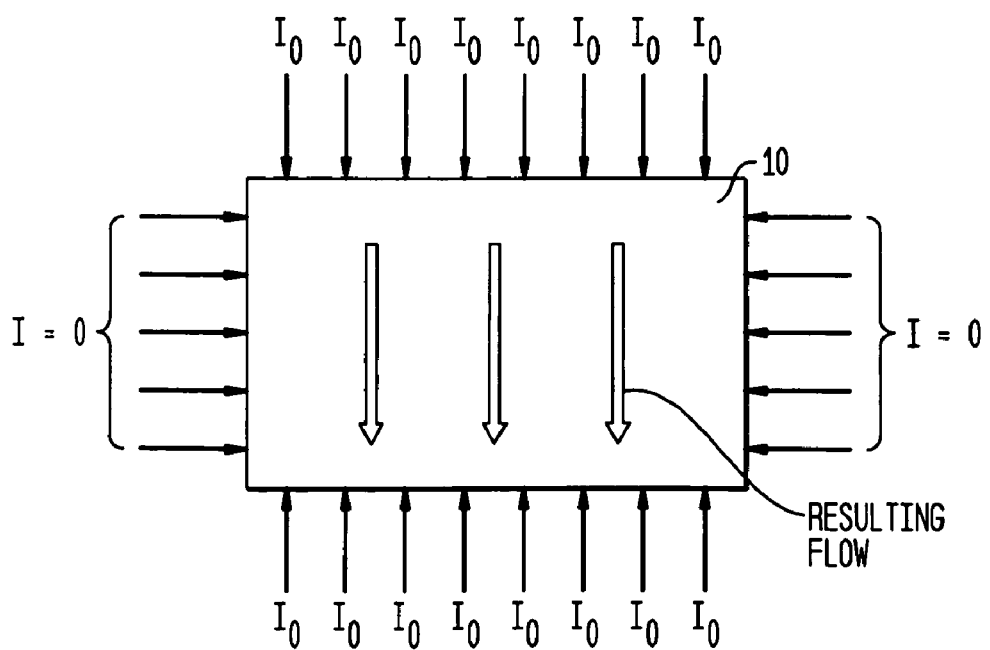
FIG. 3 is a diagram showing the generation of uniform electric fields achieved by the present invention, with resulting fields pointing in a generally veritcal direction.

As shown in FIG. 3, current sources at the right and left sides of region 10 are turned off, constant current is injected from the top of region 10, and the same amount of constant current is extracted from the bottom of region 10. According to this arrangement, a uniform electric field will be developed in a generally vertical or downward direction, as indicated by the arrows. Since the electric field is proportional to the current, the field will also be uniform and pointing generally downward.

Figure 4:
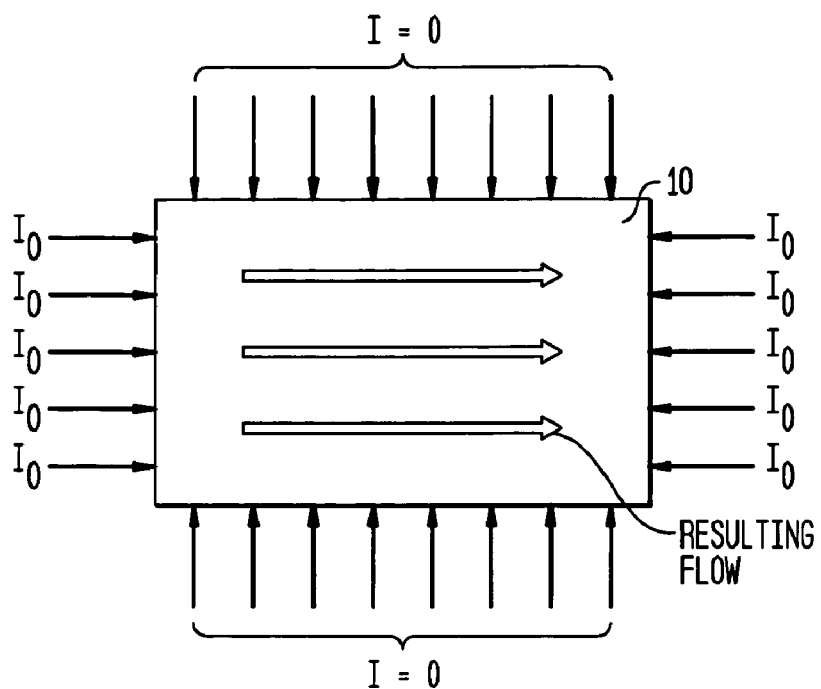
FIG. 4 is a diagram showing the generation of uniform electric fields achieved by the present invention, with resulting fields pointing in a generally horizontal direction.

As depicted in FIG. 4, an electric field can be developed in a generally rightward, horizontal direction, by turning current sources on the top and bottom of region 10 off, and by applying constant current to current sources on the left of region 10 and extracting same from current sources to the right thereof.

Figure 5:
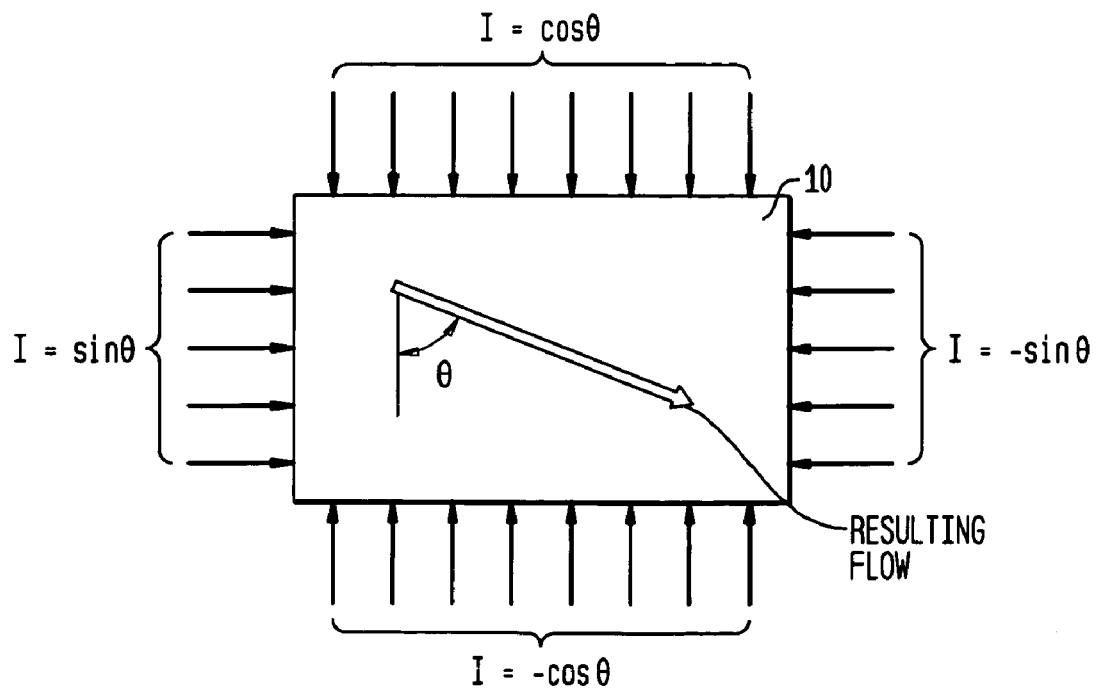
FIG. 5 is a diagram showing the generation of uniform electric fields achieved by the present invention, with resulting fields pointing generally diagonally at an angle θ.

FIG. 5 is a diagram showing the generation of uniform electric fields achieved by the present invention, with resulting fields illustratively pointing at an angle $\theta$. As shown, current can be injected or extracted from the boundaries of region 10 according to the depicted calculations. Thus, to produce fields at the angle $\theta$, current density values of $\cos\theta$, $-\sin\theta$, $-\cos\theta$, and $\sin\theta$ are applied to the top, right, bottom, and left boundaries of region 10, respectively. Where current values of I>0 exist at a given boundary (i.e., on of the four sides of region 10), current is injected at that boundary into region 10, whereas when current values of I<0 are present, current is extracted therefrom.

Figure 6A:
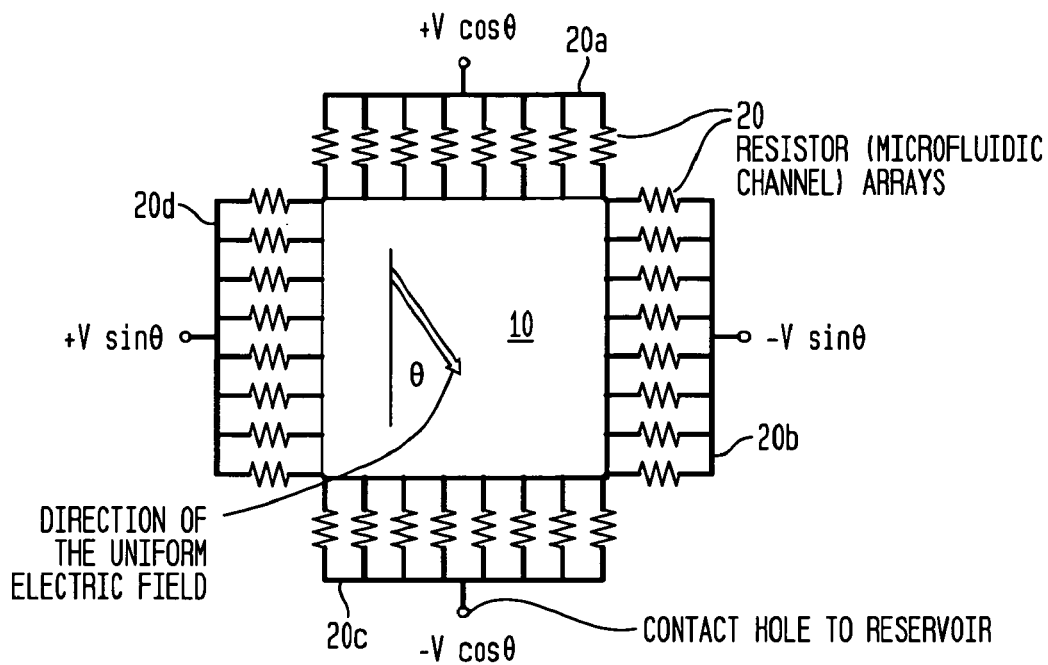
FIG. 6a is a diagram showing the current injection system of the present invention, implemented using resistor arrays.

FIG. 6a is a diagram showing the current injection system of the present invention, implemented using resistor arrays. Resistor arrays 20a, 20b, 20c, and 20d are formed by resistors connected in parallel with a voltage source. In a preferred embodiment of the invention, resistor arrays 20a-20d are formed of resistors that have high voltage drops during operation, so that all possible voltage variations in region 10 are small compared to the voltage drops of the resistors. Further, the currents flowing through the resistors of resistor arrays 20a-20d are not sensitive to output voltage variations. Therefore, the resistors operate as good current sources, and different resistors having different resistances can be connected to the same voltage source to inject varying amounts of current into region 10. Accordingly, use by the present invention of multiple resistors greatly reduces the number of voltage sources (i.e, electrodes, electrolyte reservoirs, and driving circuits) needed. Further, when fluidic microchannels are filled with electrolyte, the channels act electrically as resistors. Accordingly, fluidic microchannels can be used in place of resistor arrays 20a-20d to provide the same current injection effect.

The total resistances of each of resistor arrays 20a-20d can be set to a value n times greater than the sheet resistance of region 10, where n is usually much larger than 1. Further, the length of a side of the region 10 can be set to a. If the voltage of the top resistor array 20a is set to +V, bottom resistor array 20c set to -V, left and right resistor arrays 20b and 20d left open or grounded, a uniform electric field distribution will be established in region 10, having a field strength of approximately $2V/(a(2n+1))$ and pointing generally downward. In an alternate embodiment of the present invention, if a current of +V is applied to resistor array 20d, and a current -V is applied to resistor array 20b, while resistor arrays 20 and 20c are left open or set to ground, a uniform electric field pointing generally to the right will be produced. By applying voltages as shown in FIG. 6a, vertical and horizontal components of the electric field can be superimposed to produce a uniform electric field distribution in a direction of angle $\theta$. Thus, for a desired field distribution of angle $\theta$, voltages of $+V\cos\theta$, $-V\sin\theta$, $-V\cos\theta$, and $+V\sin\theta$ are applied to resistor arrays 20a, 20b, 20c, and 20d, respectively.

Figure 6B:
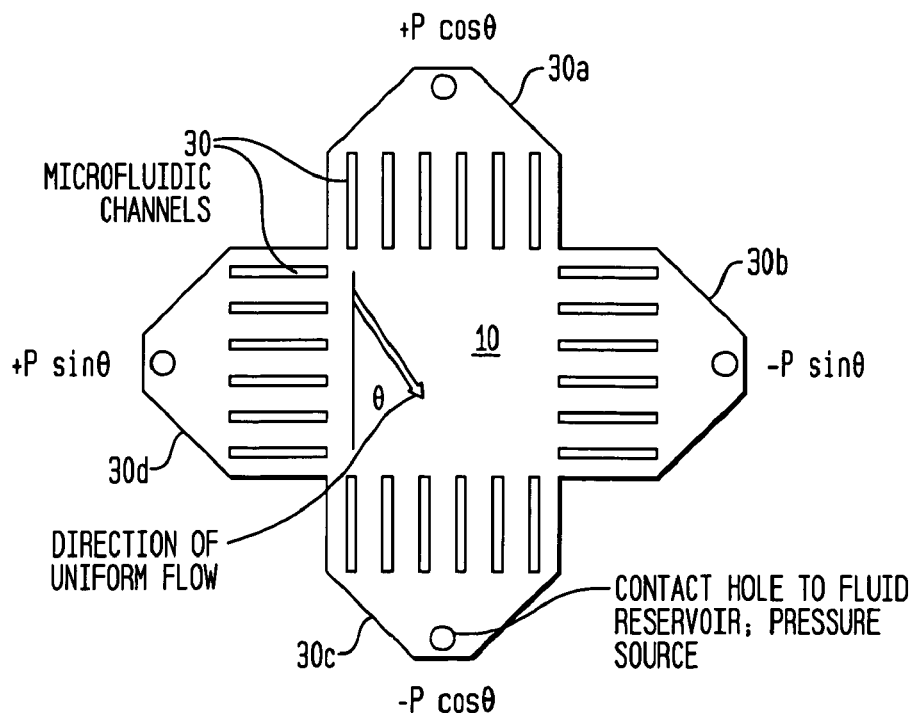
FIG. 6b is a diagram showing another embodiment of the present invention, implemented using fluidic channels.

FIG. 6b is a diagram showing another embodiment of a current injection system of the present invention, implemented using channels. The channels can be used to direct fluid therethrough ("fluidic channels"). Preferably, such channels have micron dimensions ("fluidic microchannels"), but could be of any suitable size. A plurality of channels 30, shown as channel arrays 30a-30d, serve as fluid sources connected to a pressure source. In a preferred embodiment, channels 30 are microchannels, and have high pressure drops during operation, so that any possible pressure variations within region 10 are small compared to the pressure drops of the channels 30. Fluids flowing through the channels 30 are insensitive to pressure within region 10. Therefore, channels 30 serve as good fluid current sources, and channels having varying fluidic resistances can be connected to the same pressure sources while injecting varying amounts of fluid current into region 10.

Use by the present invention of many fluidic microchannels greatly reduces the number of pressure sources (i.e., pressure regulators, "o"-rings, etc.) needed. The dimensions of channels 30 determine fluidic resistances thereof, wherein fluidic resistance is defined by the pressure drop across the channel when one unit of fluid is flowing through it. Thousands of channels 30 can be fabricated using any microfabrication technique known in the art.

The total fluidic resistances of each of channel arrays 30a-30d can be set to a value n times greater than the hydrodynamic sheet resistance of region 10, where n is usually much larger than 1. Let region 10 be a square of side a, and its conductance be C. If the hydrodynamic pressure of the top channel array 30a is set to P cos θ, right channel array 30b set to −P sin θ, bottom channel array 30c set to −P cos θ, and left channel array 30d set to P sin θ, a uniform flow distribution will be established in region 10, having a flow velocity of approximately 2PC/(a(2n+1)) and pointing in the direction of angle θ. Accordingly, by controlling the pressures of arrays 30a-d in the manner disclosed herein, a variety of flow distributions can be generated in region 10.

Importantly, FIG. 6b can also be viewed from a perspective wherein the fluidic channels link a voltage source, not shown, to the chamber. In such an embodiment, the fluidic channels function as electrical resistors and introduce electrical currents into the region in accordance with the invention as described with respect to FIGS. 4-6a. The electrical resistance of the fluidic channels can be modified by modifying the physical dimensions thereof.

Figure 7:
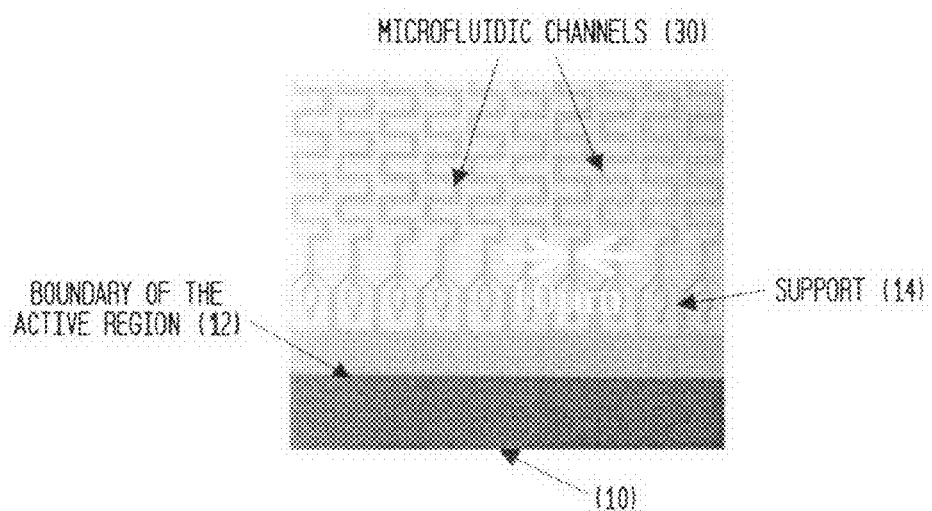
FIG. 7 is a top view showing fluidic microchannels of the present invention.

FIG. 7 is a top view showing fluidic microchannels of the present invention. The image was taken using an optical microscope. The dimensions of fluidic microchannels 30 determine both the electrical and fluidic resistances of fluid and/or electrolyte flowing therethrough. In a preferred embodiment of the present invention, fluidic microchannels 30 are 10 μm wide and 2 μm deep. Preferably, when connected to region 10 near boundary 12, fluidic microchannels 30 have widths of 100 μm near region 10. Thus, a current source is provided every 100 μm along boundary 12 of region 10. It is to be understood that other dimensions and spacings of fluidic microchannels 30 are contemplated by the present invention and are considered within the scope thereof. Supports 14 prevent the fluidic microchannels 30 from collapsing.

Injecting samples (i.e., amino acids, nucleic acids, cells, and chemicals) electrophoretically and/or hydrodynamically into a two-dimensional region in a narrow band is desirable. However, a particular problem in the art arises when very small openings are used along the boundary of the region to generate such narrow bands, as the widths of the openings do not determine the width of the band. Rather, the width of the band can be determined by electric fields lines and/or stream lines that go through the openings. Therefore, electric fields lines and/or stream lines can be generated to create narrow bands, wherein the fields lines and/or stream lines are generated in parallel to each other asymptotically. The current source method of the present invention can achieve such a result, because the fluidic microchannels thereof provide suitable openings for sample injection having uniform flows and electric fields.

In order to provide narrow-band sample injection, fluidic microchannels of the present invention can be grouped into bundles, and each bundle connected to a separate fluid reservoir and/or electrode. Then, identical fluids and/or electrolytes are introduced into the reservoirs, and a single reservoir is filled with both fluid/electrolyte and charged test samples. If the samples do not change the conductivity or viscosity of the fluid or electrolyte significantly, the presence of such samples will not perturb flow distribution or the electric field. The samples then follow the uniform flow distribution or uniform electric field to produce a narrow band. Such a methodology can be used to generate arbitrary flow distributions and electric fields having no curl or divergence in the region.

Figure 8A:
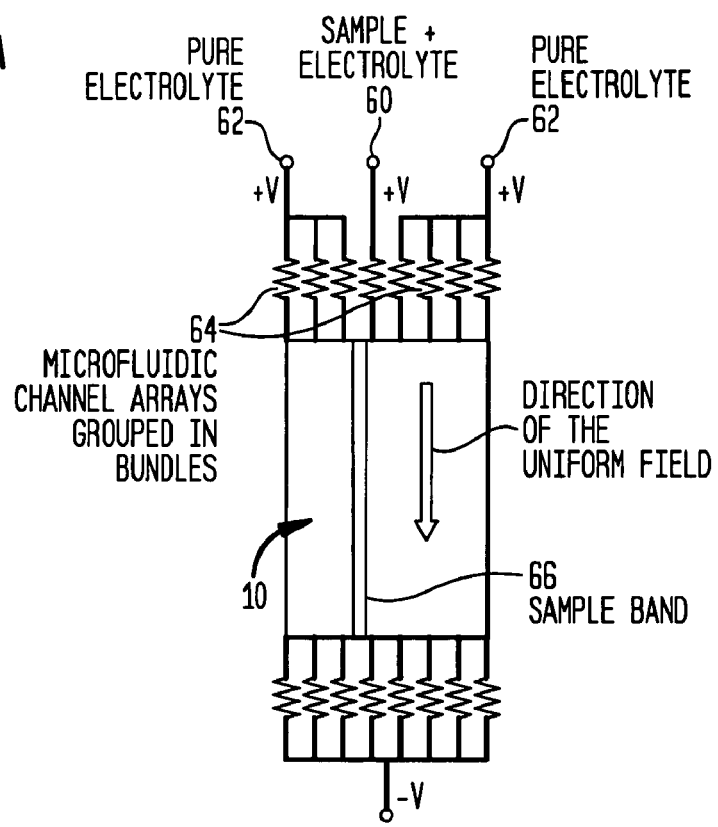
FIG. 8a is a diagram showing fluidic microchannel arrays grouped in bundles, wherein a sample and electrolyte are injected and follow electric field lines generated in the region.

FIG. 8a is a diagram showing microfluidic channel arrays grouped in bundles, wherein a sample and electrolyte are injected and follow electric field lines generated in the region to form a narrow band of the sample. Fluidic microchannel arrays 64, depicted as resistors, are grouped in bundles and have identical resistances. Because the fluidic microchannel arrays 64 inject constant current from the top, and an equal amount of current is extracted from the bottom, the electric field inside of region 10 is uniform and pointing generally downward. One of the fluidic microchannel arrays 64 contains a test sample 60 and electrolyte. The remaining fluidic microchannel arrays 64 contain only pure electrolyte 62. Because the test sample 60 follows the uniform field lines of region 10, a narrow sample band 66 is produced.

Figure 8B:
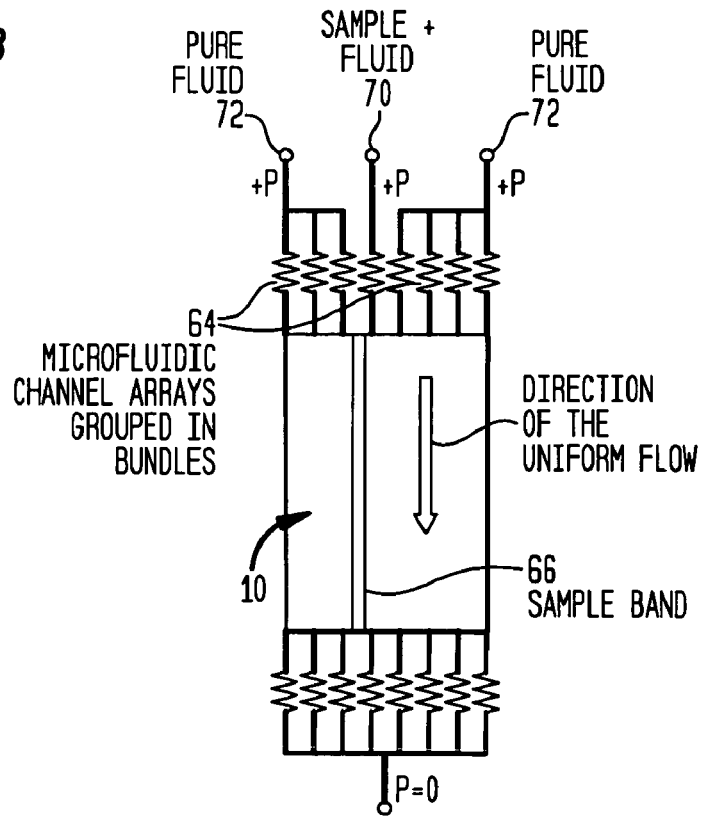
FIG. 8b is a diagram showing fluidic microchannel arrays grouped in bundles, wherein a sample and pure fluid are injected and follow stream lines generated in the region.

FIG. 8b is a diagram showing fluidic microchannel arrays grouped in bundles, wherein a sample and fluid are injected and follow uniform flow distributions generated in the region to form a narrow band of the sample. Fluidic microchannel arrays 64, depicted as resistors, are grouped in bundles and have identical fluidic resistances. Because the fluidic microchannel arrays 64 inject constant current from the top, and an equal amount of current is extracted from the bottom, the flow inside of region 10 is uniform and pointing generally downward. One of the fluidic microchannel arrays 64 contains a test sample 70 and a fluid. The remaining fluidic microchannel arrays 64 contain only pure fluid 72. Because the test sample 70 follows the flow streamlines of region 10, a narrow sample band 66 is produced.

The present intention also allows for the generation of arbitrary electric field and fluidic distributions. As discussed earlier, uniform electric fields and flow distributions can be generated by fluidic microchannels having identical dimensions. To generate arbitrary electric fields and flow distributions, the present invention can be adapted to provide fluidic microchannels having varying dimensions, and accordingly, varying electric and fluidic resistances.

Figure 9A:
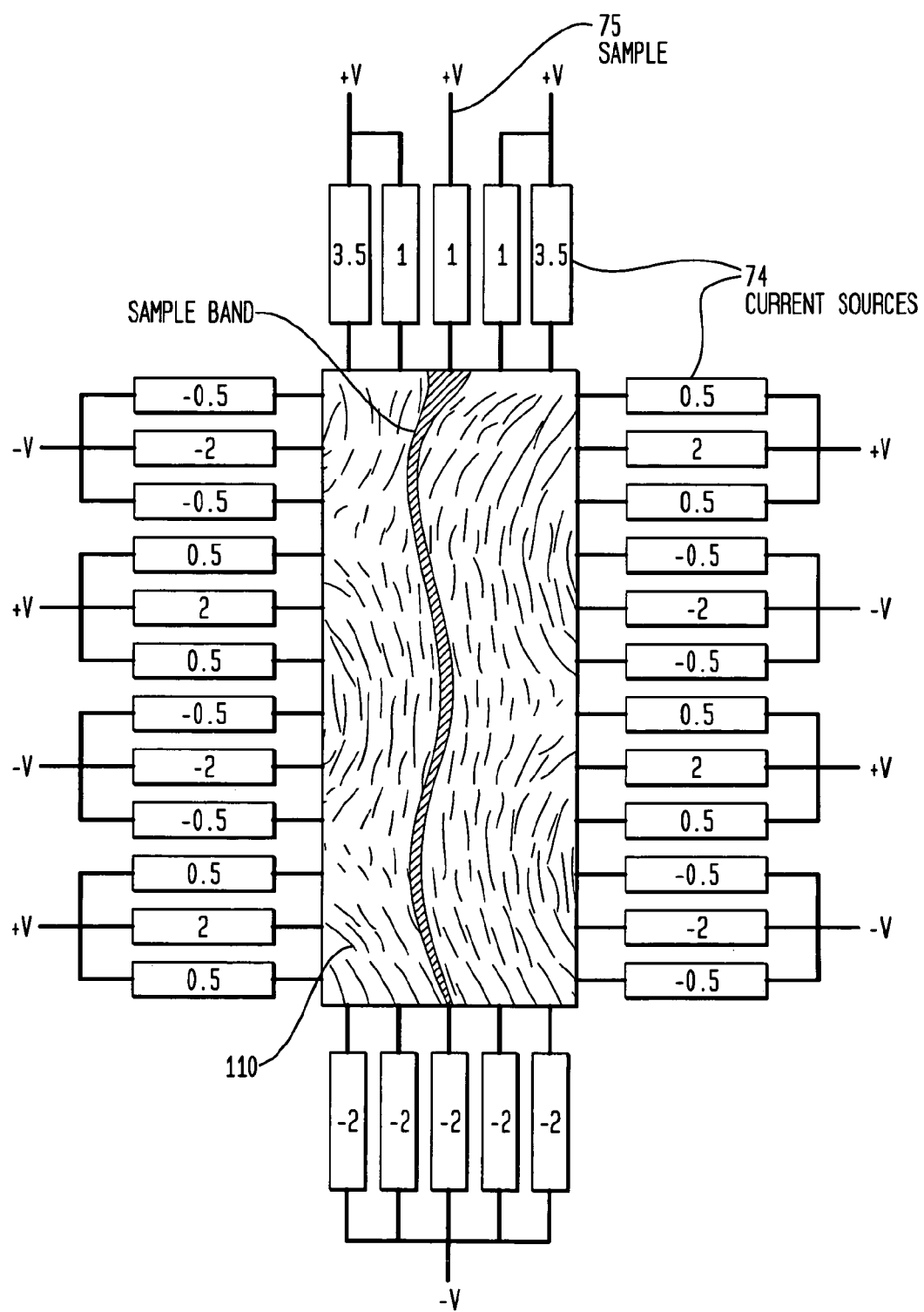
FIG. 9a is a diagram showing the generation of a complex field pattern and a test sample band using fluidic microchannel arrays, a sample, and electrolyte.

FIG. 9a is a diagram showing the generation of an arbitrary test sample band using microfluidic channel arrays, a sample, and an electrolytic solution. A wavy electric field distribution is produced in a rectangular region 110, using a plurality of current sources 74. The amount of current injected into the region is shown as arbitrary units −2, −0.5, 0.5, and 2. All reservoirs contain electrolyte. Reservoir 75 contains both electrolyte and a quantity of test sample. The arrows in the region 110 indicate the resulting electric field. Since the test sample follows the electric field, a tapered and winding band of test sample is formed.

Figure 9B:
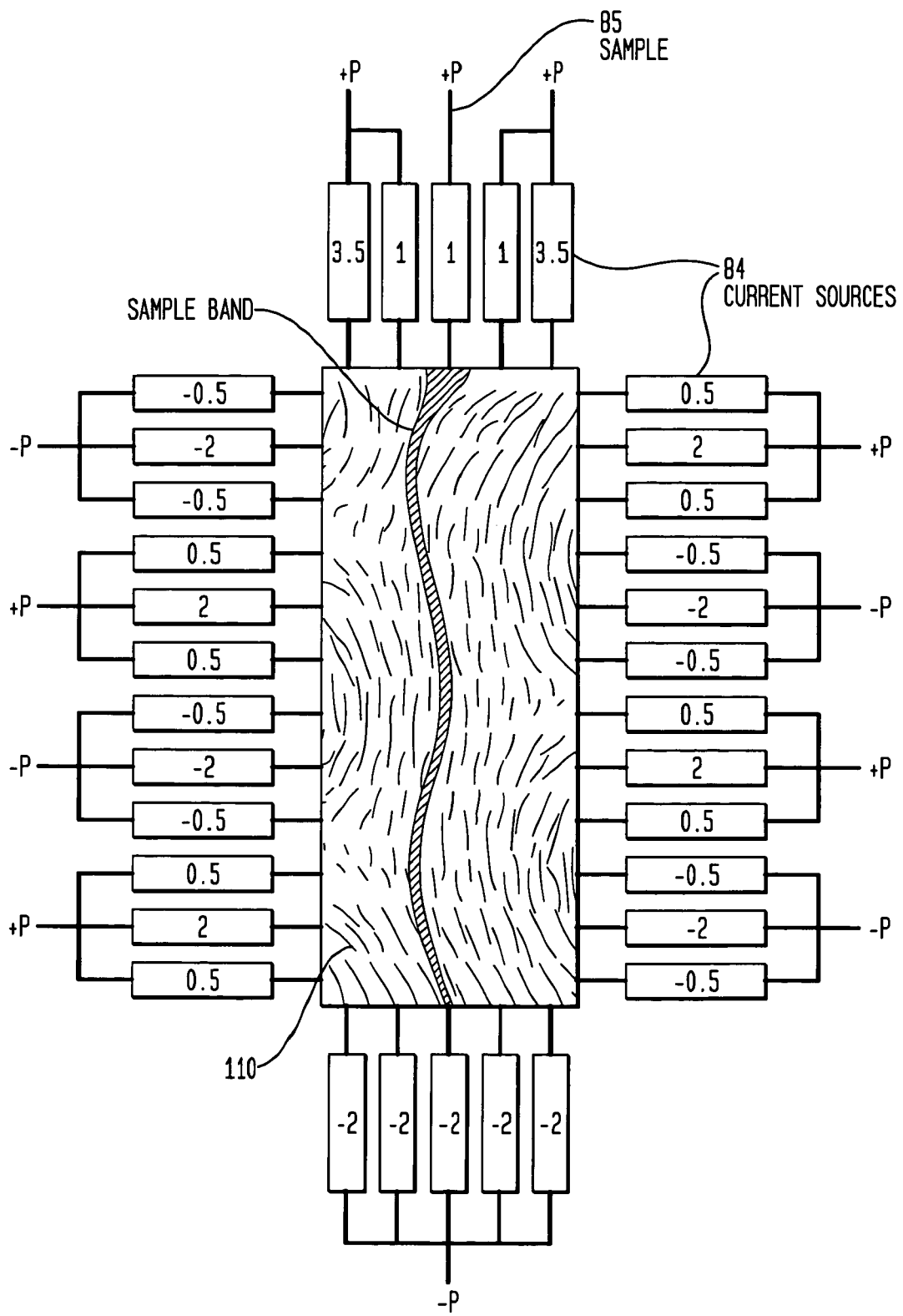
FIG. 9b is a diagram showing an alternate method for generating a complex flow pattern and a sample band using fluidic microchannel arrays, a sample, and pure fluid.

FIG. 9b is a diagram showing an alternate method for generating an arbitrary test sample band using fluidic microchannel arrays, a sample, and pure fluid. A similar wavy test sample distribution is produced in a rectangular region 110, using a plurality of current sources 84. The amount of current injected into the region is shown as arbitrary units −2, −0.5, 0.5, and 2. All reservoirs contain pure fluid. Reservoir 85 contains both pure fluid and a quantity of test sample. The arrows in the region 110 indicate the resulting fluid flow. Since the test sample follows the flow distribution, a tapered and winding band of test sample is formed.

Figure 10:
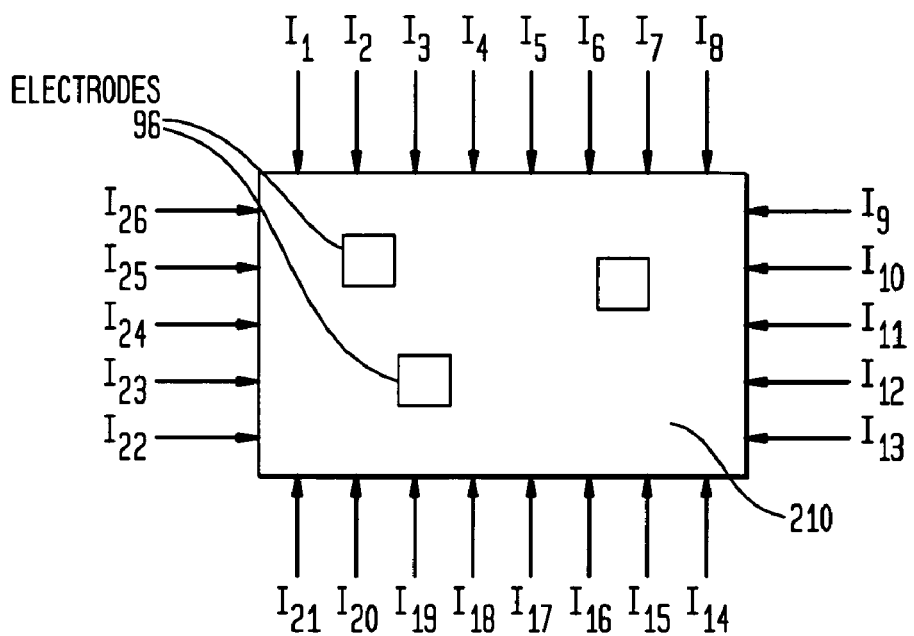
FIG. 10 is a diagram showing a modified region and charge injection system according to the present invention, wherein electrodes are introduced into the region to provide an electric field having no divergence or curl.

FIG. 10 is a diagram showing a modified region and charge injection system according to the present invention, wherein electrodes are introduced into the region to provide an electric field having divergence. Electrodes 96 allow for the generation of fields that have divergence, and can be disposed anywhere within region 210. Further, electrodes 96 can be designed as current sources or voltage sources.

Figure 11:
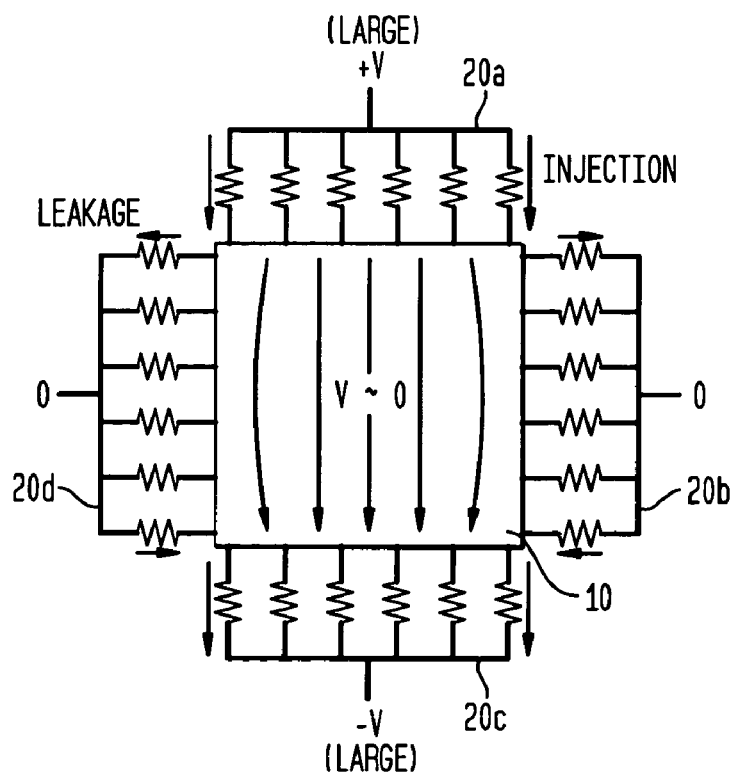
FIG. 11 is a diagram showing the current injection method of the present invention using resistor arrays.
Figure 12:
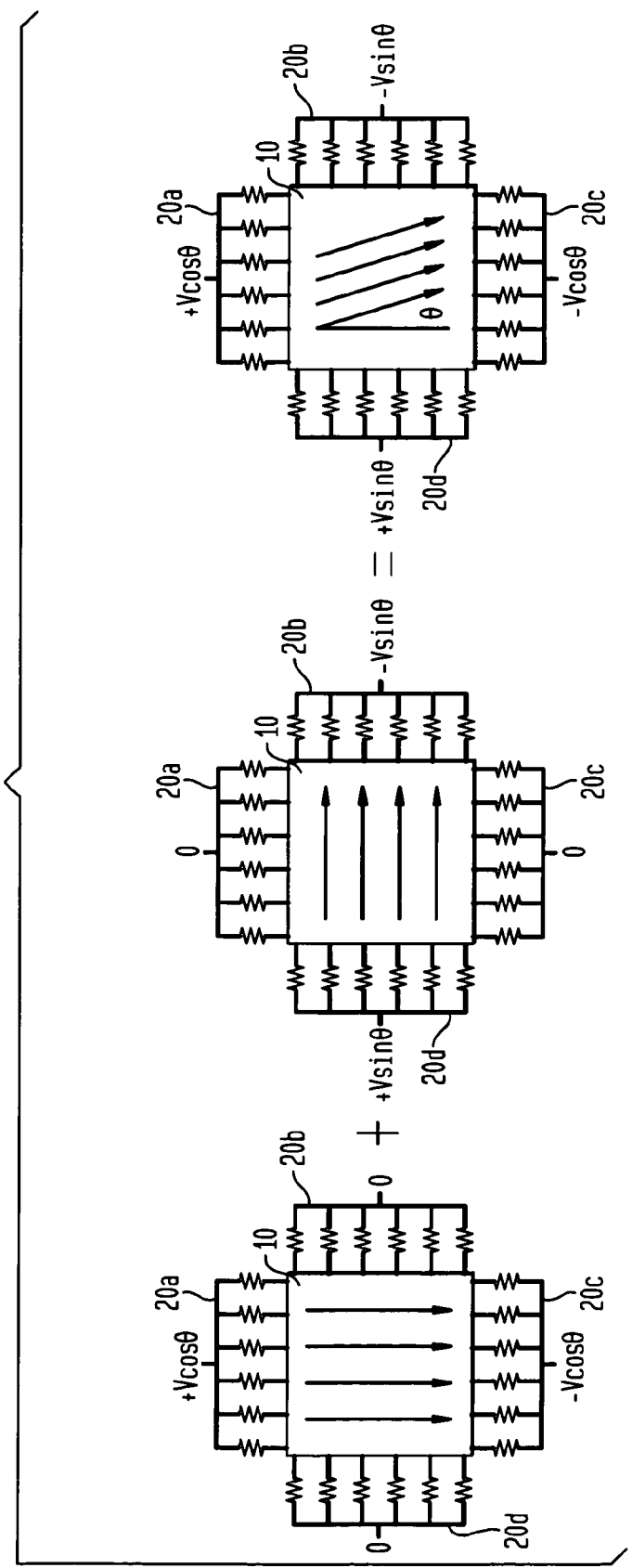
FIG. 12 is a diagram showing the superimposition principle for generating uniform fields at arbitrary directions.

FIG. 11 is a diagram showing the current injection method of the present invention using resistor arrays 20a, 20b, 20c, and 20d. In a preferred embodiment of the invention, fluidic microchannels fabricated from fused silica glass form the resistors. The channels connect the area 10 to buffer reservoirs, where voltage is applied through immersed contacts. The electrical resistances of the channels are controlled by their dimensions. The injected vertical current for each resistor of array 20a is approximately the large voltage drop divided by its resistance, which, to the first order, is a constant. The current leakage through the resistors of arrays 20b and 20d is negligible, because the voltage drop across the resistors is small. In the limit where the resistance approaches infinity, the field inside the area 10 is perfectly uniform. Because horizontal fields can similarly be generated, fields at any orientation can be created using superimposition of conditions for horizontal and vertical fields, as shown in FIG. 12. Thus, any field having a desired angle θ can be generated, where input conditions of V cos θ, –V sin θ, –V cos θ, and V sin θ are present at arrays 20a-20d, respectively.

Figure 1A:
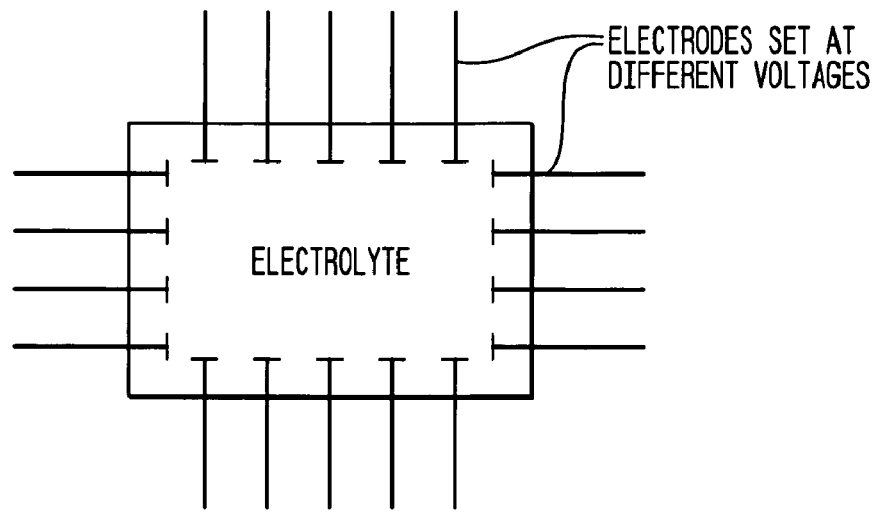
FIG. 1a is a diagram showing a prior art device for generating contour-clamped homogenous electric fields ("CHEF").
Figure 1B:
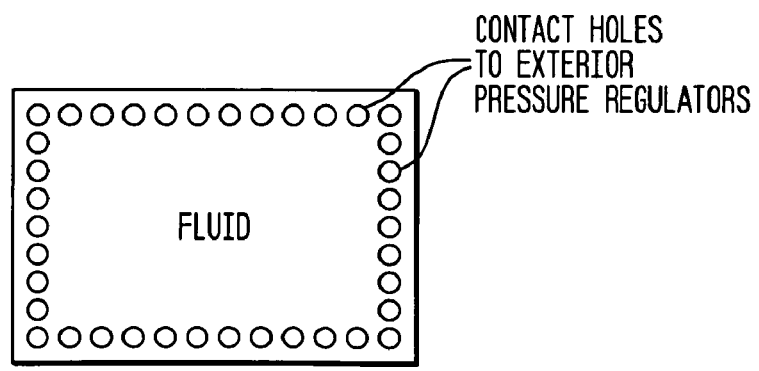
FIG. 1b is a diagram showing a prior art device for generating flow distributions in a region.

The residual non-uniformity of the generated field can be characterized by the root-mean-square ("RMS") field distortion, defined as:

$$\sqrt{\frac{\iint\limits_{\substack{array\\area}} |E - E_0|^2 \, dx\,dy}{\iint\limits_{\substack{array\\area}} |E_0|^2 \, dx\,dy}} \quad (1)$$

where E is the field to be calculated and $E_0$ is the ideal uniform field. The vertical field generated by a typical 24-electrode CHEF system, similar to the system of FIG. 1a, has an RMS distortion of approximately 9%, based upon computer simulation using Equation 1 and a Laplace equation that governs the electric field. Most distortions in such systems occur in regions near the electrodes.

Figure 13A:
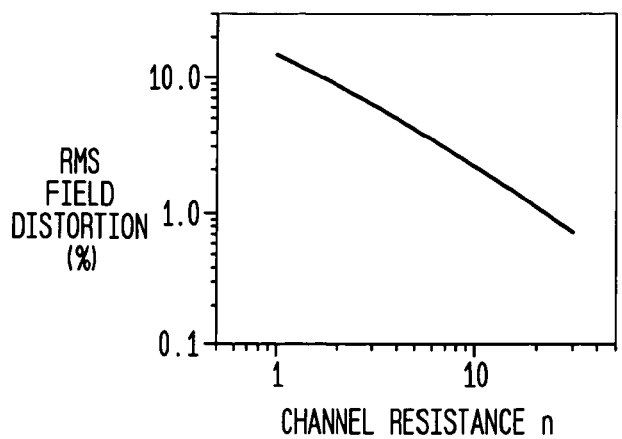
FIG. 13a is a graph comparing calculated root-mean-square ("RMS") field distortion as a function of channel resistance.
Figure 13B:
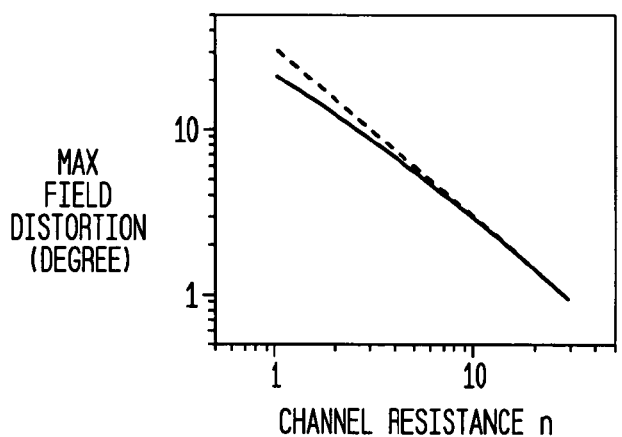
FIG. 13b is a graph comparing maximum field distortions between an actual field and a homogenous field as functions of channel resistance.
Figure 14:
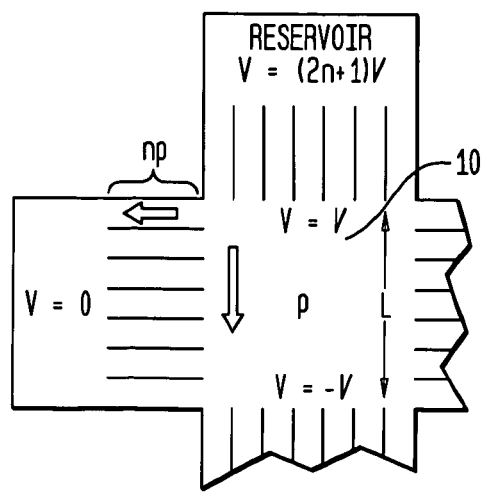
FIG. 14 is a diagram showing a region having channels surrounding the region.

FIGS. 13a, 13b show evaluation results of the present invention using an exemplary device depicted in FIG. 14. To evaluate the uniformity of the electric fields generated by the current injection method of the present invention, it is assumed that the total electrical resistance of channels in parallel on each side of the area 10 of device of FIG. 14 is nρ, where ρ is the sheet resistance of area 10 and n is a positive number. Computer simulation shows that the field is made uniform as the channel resistance increases, as depicted in the graph of FIG. 13a. In terms of the RMS field distortion, the current injection method of the present invention out performs the CHEF method when n>2.1. The distortion is largest at the four corners of area 10 when vertical fields are produced.

The maximum angle of the generated vertical field with respect to an ideal vertical direction is shown in the graph of FIG. 13b. The curve shown therein approaches 1/(2n) as n increases. In this situation, at the corners of area 10, the horizontal component of the current density is V/(nρL), where V is the electric potential at the corner, and L is the length of area 10. Similarly, the vertical component of the current density is approximately 2V/(ρL). The angle of the field at the corner with respect to the vertical axis is approximately the ratio of the two components, or 1/(2n). Thus, the field is made uniform by choosing a large value for n. Because a large fraction of the applied voltages is then dropped over the resistor arrays, a uniform field is produced at the expense of its strength for a given set of applied voltages. Such a condition, however, is not detrimental in fluidic chip applications, because such devices are generally fabricated to be small.

Figure 15:
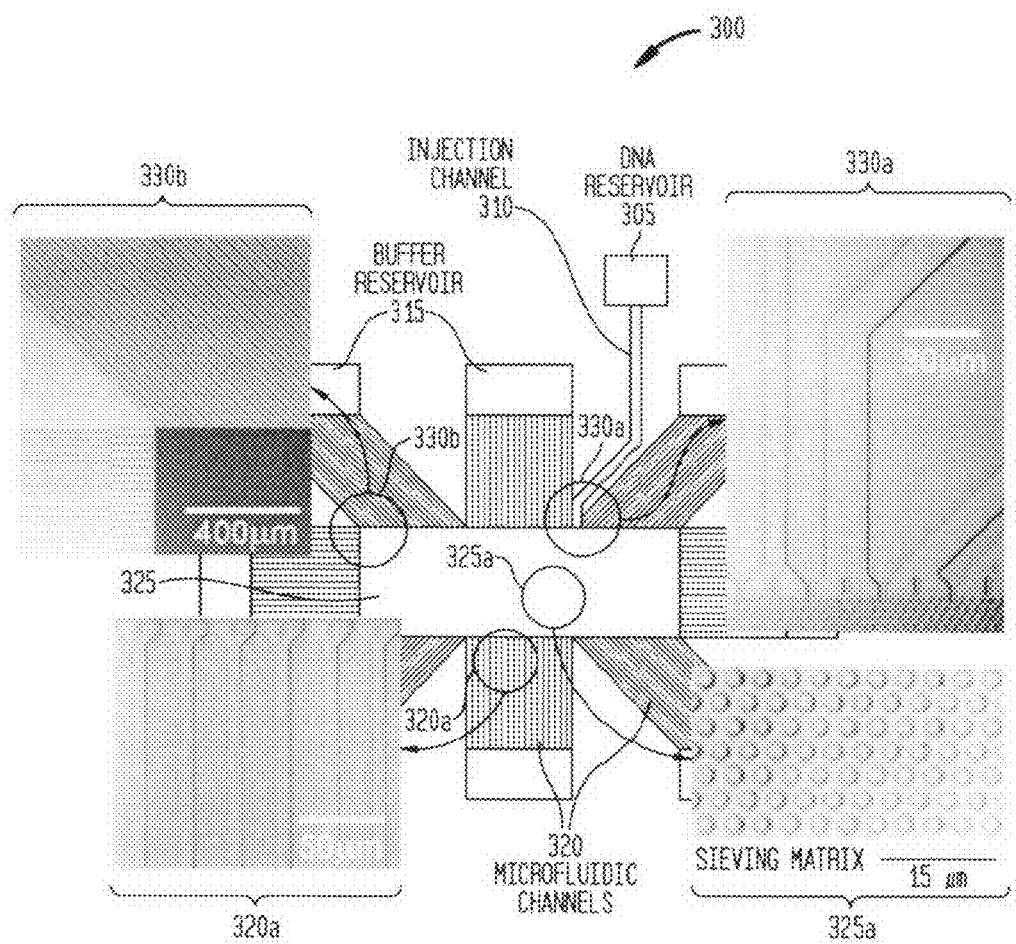
FIG. 15 is a top view of the DNA separation and movement apparatus of the present invention.

FIG. 15 is a top view of the DNA separation and/or movement apparatus according to the present invention. Device 300 utilizes the above-mentioned electric field, flow distribution, and current injection methods, and can be microfabricated on fused silica using lithography or other processes known in the art. Device 300 comprises a sieving matrix 325, to which a plurality of buffer reservoirs 315 are connected via fluidic microchannels 320. DNA stored in DNA reservoir 305 is injected into sieving matrix 325 via injection channel 310.

Sieving matrix 325, shown in greater detail in view 325a, is a two-dimensional array of microposts. In a preferred embodiment of the present invention, the microposts of sieving matrix 325 are manufactured to a size comparable to that of a DNA molecule in the approximately 100 kbp range as a random coil. Additional sizes are considered within the scope of the invention. Under direct current (DC) fields, DNA molecules do not interact with the microposts of sieving matrix 325, and migrate at a constant mobility, independent of their molecular weights. It has been shown that when fields introduced to such DNA molecules alternate between two directions about 120 degrees apart, the average migration mobility becomes dependent on molecular weight, providing a basis on which to separate DNA of different sizes. Such a phenomenon occurs when DNA molecules become stretched and interact with the microposts. Larger molecules tangle around the microposts and, accordingly, have lower mobilities.

The fluidic microchannels 320, shown in greater detail in view 320a, surround the sieving matrix 325 and connect same to a plurality of buffer reservoirs 315. The interface between sieving matrix 325 and fluidic microchannels 320 is shown in detail in view 330b. Buffer reservoirs 315 are connected to voltage sources, wherein voltages are applied. DNA molecules are injected into the array from injection channel 310 (shown in greater detail in view 330a), connecting DNA reservoir 305 to sieving matrix 315. In a preferred embodiment of the invention, eight buffer reservoirs 315 are provided to reduce the resistance needed for a given uniformity goal. The resistance of each bundle of fluidic microchannels 320 connecting each buffer reservoir 315 to sieving matrix 325 is determined, in a preferred embodiment, to be 2.2 times as large as the sheet resistance of sieving matrix 325 (n=2.2). It is to be understood that different quantities of reservoirs and/or channel resistances are considered within the scope of the invention. Computer simulation, using Equation 1, above, shows that the RMS field distortion of device 300 is approximately 1% around the center section of sieving matrix 325, where DNA is injected and fractionated.

The fabrication process of device 300 can be accomplished in a single lithographic step defining the posts and channels of the device. The pattern can be transferred anisotropically to a fused silica substrate with reactive ion etching ("RIE") using $CF_4$ and $H_2$. In a preferred embodiment, the etch depth is up to 6 μm. Other substrates and etch depths are considered within the scope of the invention. Access holes contacting the external reservoirs can be mechanically drilled. The substrate can be tightly bonded to a piece of glass cover slip to form enclosed fluidic channels. It is to be understood that other fabrication processes known in the art can be used to fabricate device 300.

Figure 16A:
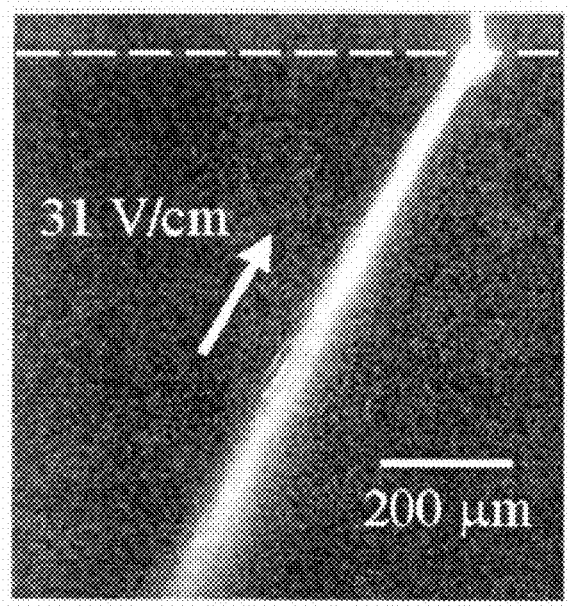
FIGS. 16a, 16b, and 16c show fluorescent microscopy views of DNA separation and movement using the microfabricated device of the present invention.
Figure 16B:
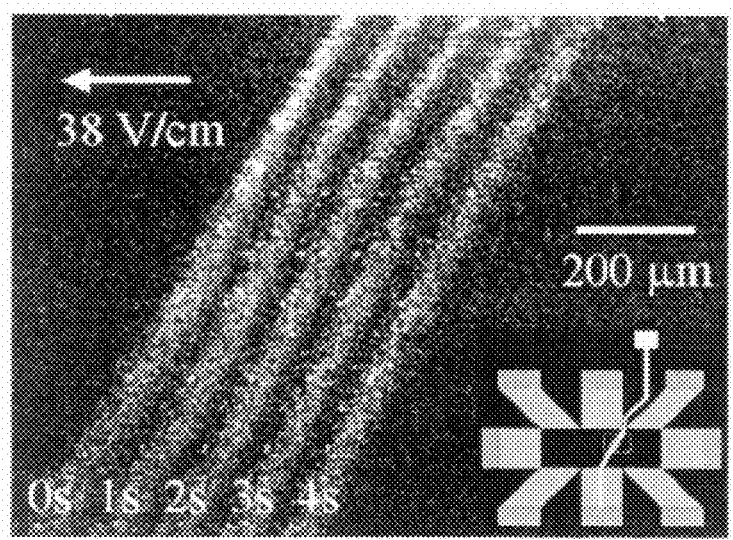
Figure 16C:
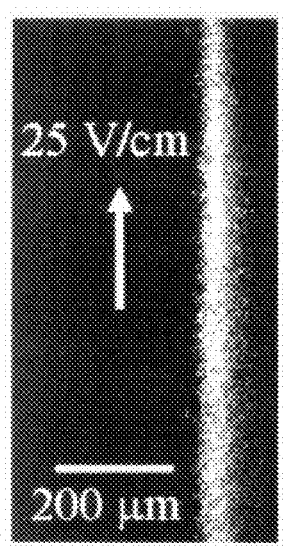

FIGS. 16a, 16b, and 16c shows fluorescent microscopy views of DNA separation using the microfabricated device 300 of the present invention. Device 300 was used to generate fields at 0°, 60°, and 90° with respect to the horizontal axis. As seen in FIG. 16a, DNA was injected into the device at 60°.

The dashed line marks the boundary of the array (i.e., an edge of sieving matrix 125). DNA molecules were stained with fluorescent dye, and observed with an optical microscope. A 60° electric field of 31 V/cm was applied. The DNA molecules formed a straight band as they traveled along the electric field, with the maximum deviation for the desired angle of approximately 2°. Then, as shown in FIG. 16*b*, the field was switched to a horizontal orientation. The band was moved at a constant speed in the horizontal direction, and the trajectories of the molecules revealed that the field was strictly horizontal. Spatial uniformity of the electric field is shown through the steady motion of the band. The left-most band (0 s) was produced after DNA injection using an electric field of −30° with respect to vertical (52 V/cm), and the four right bands were produced at one second intervals with fields of 38 V/cm in the horizontal direction. As shown in FIG. 16*c*, DNA injection at 90° produced a straight band. Accordingly, the methodology and apparatus of the invention produces uniform fields over a large area at multiple angles.

Figure 17A:
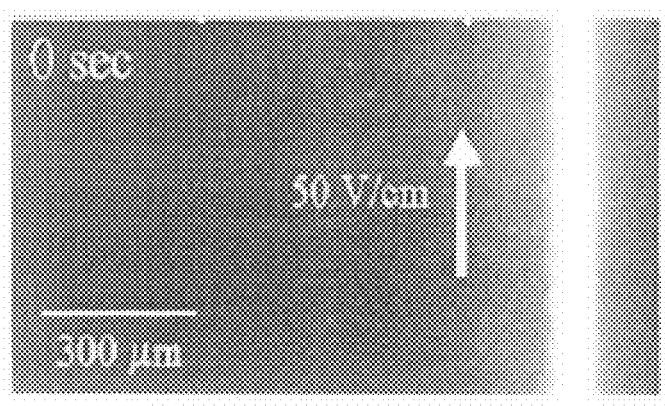
FIGS. 17a, 17b, and 17c show sequential fluorescent microscopy views of DNA separation using the microfabricated device of the present invention.
Figure 17B:
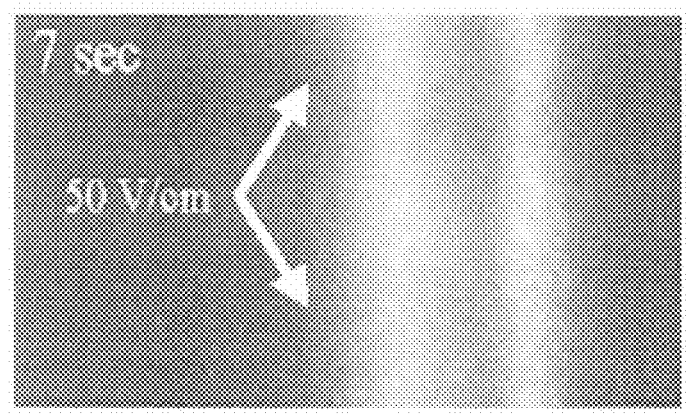
Figure 17C:
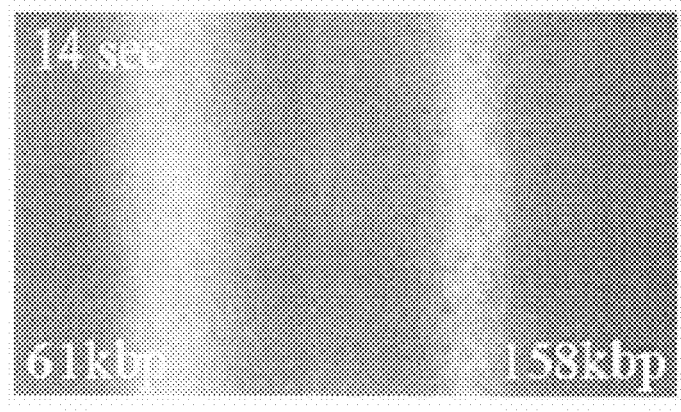

The device of the present invention was experimentally tested with bacterial artificial chromosomes ("BAC") to demonstrate its capability of separating genomic DNA. The results of such testing are depicted in the fluorescent microscopy views of the device in FIGS. 17*a*, 17*b*, and 17*c*. BACs are a class of recombinant DNA that play a key role in genomic projects. The BACs were isolated and purified from transformed *E. Coli*. strains, using miniprep protocols. 61 kbp and 158 kbp of BAC (18 μm and 54 μm long, respectively) were mixed and injected into the array by a vertical field, as shown in FIG. 17*a*. The field was then switched alternatively between +60° and −60° with respect to the horizontal axis to separate DNA, as shown in FIG. 17*b*. The DNA then migrated toward the average field direction. In less than 7 seconds, the 61 kbp DNA was cleanly separated from the 158 kbp molecules, as shown in FIG. 17*c*, a result that is well over three orders of magnitude faster than the conventional PFGE method. The resolution, defined as the full width of the half maximum of a band, is approximately 77 kbp at 7 seconds, and approximately 36 kbp at 14 seconds.

Having thus described the invention in detail, it is to be understood that the foregoing description is not intended to limit the spirit and scope thereof. What is desired to be protected by Letters Patent is set forth in the appended claims.

What is claimed is:

1. An apparatus for separating molecules comprising:
a region for receiving the molecules to be separated;
a first set of microfluidic resistors connected to opposing sides of the region for injecting a first electrical current into the region; and
a second set of microfluidic resistors connected to opposing sides of the region for injecting a second electrical current into the region simultaneously with the first electrical current;
wherein the apparatus is configured to apply the first and second electrical currents simultaneously to create a uniform electric field across the region orientable at a plurality of angles for separating the molecules.

2. The apparatus of claim 1, wherein the uniform electric field separates the molecules according to size.

3. The apparatus of 1, wherein one of the first and second sets of microfluidic resistors comprises fluidic microchannels.

4. The apparatus of claim 1, wherein the molecules are DNA molecules.

5. The apparatus of claim 1, wherein the first and second sets of microfluidic resistors having a resistance greater than a resistance of the region.

6. The apparatus of claim 1, wherein the first and second electrical currents are constant.

7. The apparatus of claim 1, wherein the first and second sets of microfluidic resistors control normal components of the first and second electrical currents.

8. The apparatus of claim 1, further comprising at least one sample reservoir for storing the molecules prior to separation.

9. The apparatus of claim 8, further comprising at least one injection channel connected between the sample reservoir and the region for injecting the molecules into the region.

10. The apparatus of claim 1, further comprising at least one buffer reservoir for storing the molecules after separation.

11. The apparatus of claim 10, further comprising at least one fluidic microchannel connected between the at least one buffer reservoir and the region for channeling the molecules to the at least one buffer reservoir after separation.

12. The apparatus of claim 1, wherein one of the first set of microfluidic resistors is connected to a first voltage source of +V sin θ, where θ corresponds to a resultant angle of the uniform electric field in the region.

13. The apparatus of claim 12, wherein the other of the first set of microfluidic resistors is connected to a second voltage source of −V sin θ, where θ corresponds to the resultant angle of the uniform electric field in the region.

14. The apparatus of claim 13, wherein one of the second set of microfluidic resistors is connected to a third voltage source of +V cos θ, where θ corresponds to the resultant angle of the uniform electric field in the region.

15. The apparatus of claim 14, wherein the other of the second set of microfluidic resistors is connected to a fourth voltage source of −V cos θ, where θ where θ corresponds to the resultant angle of the uniform electric field in the region.

16. An apparatus for generating electric fields in a fluid for separating molecules comprising:
a region for receiving the molecules to be separated;
a first set of fluidic channels connected to opposing sides of the region for injecting a first electrical current into the region; and
a second set of fluidic channels connected to opposing sides of the region for injecting a second electrical current into the region simultaneously with the first electrical current,
wherein the apparatus is configured to apply the first and second electrical currents simultaneously to create a uniform electric field across the region orientable at a plurality of angles for separating the molecules.

17. The apparatus of claim 16, wherein the molecules are separated electrophoretically.

18. The apparatus of claim 16, wherein the molecules are DNA molecules.

19. The apparatus of claim 16, wherein the first and second sets of fluidic channels have at least one electric resistance.

20. The apparatus of claim 19, wherein the at least one electric resistance is dependent upon a dimension of at least one of the fluidic channels.

21. The apparatus of claim 16, wherein the first and second sets of fluidic channels have at least one fluidic resistance.

22. The apparatus of claim 21, wherein the at least one fluidic resistance is dependent upon a dimension of at least one of the fluidic channels.

23. The apparatus of claim 21, wherein the fluidic channels establish a uniform flow distribution in the region.

24. The apparatus of claim 23, wherein the uniform flow distribution is orientable at any angle.

25. The apparatus of claim 16, wherein the first and second electrical currents arc constant.

26. The apparatus of claim 16, wherein the first and second sets of fluidic channels control normal components of the first and second electrical currents.

27. The apparatus of claim 16, further comprising at least one sample reservoir for storing the molecules prior to separation.

28. The apparatus of claim 27, further comprising at least one injection channel connected between the sample reservoir and the region for injecting the molecules into the region.

29. The apparatus of claim 16, further comprising at least one buffer reservoir for storing the molecules after separation.

30. The apparatus of claim 29, further comprising at least one fluidic channel connected between the at least one buffer reservoir and the region for channeling the molecules to the at least one buffer reservoir after separation.

31. The apparatus of claim 16, wherein one of the first set of fluidic channels is connected to a first voltage source of $+V \sin \theta$, where $\theta$ corresponds to a resultant angle of the uniform electric field in the region.

32. The apparatus of claim 31, wherein the other of the first set of fluidic channels is connected to a second voltage source of $-V \sin \theta$, where $\theta$ corresponds to a resultant angle of the uniform electric field in the region.

33. The apparatus of claim 32, wherein one of the second set of fluidic channels is connected to a third voltage source of $+V \cos \theta$, where $\theta$ corresponds to the resultant angle of the uniform electric field in the region.

34. The apparatus of claim 33, wherein the other of the second set of fluidic channels is connected to a fourth voltage source of $-V \cos \theta$, where $\theta$ corresponds to the resultant angle of the uniform electric field in the region.

35. An apparatus for separating molecules comprising:
a region for receiving molecules to be separated; and
a plurality of microfluidic resistors interconnected with a peripheral edge of the region, the plurality of microfluidic resistors simultaneously injecting first and second electrical currents into the region,
wherein the apparatus is configured to apply the first and second electrical currents simultaneously to create a uniform electrical field in the region selectively orientable at a plurality of angles for separating the molecules.

36. The apparatus of claim 35, wherein the plurality of microfluidic resistors comprise fluidic microchannels.

37. The apparatus of claim 35, wherein the plurality of microfluidic resistors comprise constant current sources.

38. An apparatus for generating electric fields in a fluid for separating molecules comprising:
a region for receiving the molecules to be separated;
first means for injecting a first electrical current into the region, the first means connected to a first set of opposing sides of the region; and
second microfluid means for injecting a second electrical current into the region simultaneously with the first electrical current, the second microfluid means connected to a second set of opposing sides of the region,
wherein the apparatus is configured to apply the first and second electrical currents simultaneously to create a uniform electric field in the region orientable at a plurality of angles for separating the molecules.

39. The apparatus of claim 38, wherein the first and said second microfluid means for injecting currents each comprise microfluidic resistors.

40. The apparatus of claim 39, wherein the first and said second electrical currents are constant.

41. The apparatus of claim 38, wherein the first and said second microfluid means for injecting currents each comprise fluidic microchannels.

42. The apparatus of claim 41, wherein the fluidic microchannels generate a uniform fluid flow distribution in the region.

* * * * *

UNITED STATES PATENT AND TRADEMARK OFFICE
CERTIFICATE OF CORRECTION

PATENT NO. : 7,597,791 B2
APPLICATION NO. : 10/147370
DATED : October 6, 2009
INVENTOR(S) : Lotien Richard Huang, James Christopher Sturm and Robert Hamilton Austin It is certified that error appears in the above-identified patent and that said Letters Patent is hereby corrected as shown below:

On the title page, item [56] in the References Cited Section, on Page 2 of the patent, in the first column under Other Publications, the second to last reference, the completed date of the Preliminary Examination Report reads "Jun. 2004," however, the date should read "Jun. 9, 2004."

In the References Cited Section, on Page 2 of the patent, in the second column under Other Publications, the sixth reference, namely, the Office Action dated October 10, 2007, is from Application No. 11/075,682, however, the issued patent lists the Application No. as "11/015,682."

Column 5, line 29, the first appearance of the word "region" should be deleted.

Column 8, line 29, the word "intention" should be deleted, and should be replaced with the word "invention."

Column 14, line 14, the word --microfluidic-- should be inserted after the first occurrence of the word "first."

Column 14, line 15, the word --microfluidic-- should be inserted after the first occurrence of the word "first."

Signed and Sealed this

Thirteenth Day of April, 2010

David J. Kappos
*Director of the United States Patent and Trademark Office*